(12) United States Patent
Doona et al.

(10) Patent No.: US 8,133,449 B2
(45) Date of Patent: *Mar. 13, 2012

(54) PORTABLE CHEMICAL STERILIZER

(75) Inventors: Christopher Doona, Oxford, MA (US);
Maria Curtin, Easton, MA (US);
Florence Feeherry, Wellesley, MA (US); Satish Kanlikar, Rochester, NY (US); Kenneth Kustin, San Diego, CA (US); Irwin Taub, Framingham, MA (US); Barbara Taub, legal representative, Framingham, MA (US); David Baer, San Antonio, TX (US); Albert McManus, Floresville, FL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 308 days.

This patent is subject to a terminal disclaimer.

(21) Appl. No.: 12/494,701

(22) Filed: Jun. 30, 2009

(65) Prior Publication Data

US 2009/0304555 A1    Dec. 10, 2009

Related U.S. Application Data

(60) Division of application No. 11/105,211, filed on Apr. 13, 2005, now Pat. No. 7,625,533, which is a continuation-in-part of application No. 10/988,442, filed on Nov. 10, 2004, now Pat. No. 7,883,640.

(51) Int. Cl.
*A61L 2/00* (2006.01)
*A61L 9/00* (2006.01)
*B01J 7/00* (2006.01)

(52) U.S. Cl. ........ 422/292; 422/295; 422/297; 422/300; 422/305

(58) Field of Classification Search .................. 422/292, 422/295, 305, 112, 297, 300
See application file for complete search history.

(56) References Cited

U.S. PATENT DOCUMENTS

| | | | | |
|---|---|---|---|---|
| 3,445,039 A * | 5/1969 | Corini et al. | .................. | 222/640 |
| 3,557,840 A * | 1/1971 | Maybee | ........................ | 138/149 |
| 3,814,003 A * | 6/1974 | Vacano | .......................... | 99/276 |
| 4,164,853 A * | 8/1979 | McDonough | ................ | 62/457.1 |
| 4,697,070 A | 9/1987 | Kai | | |
| 4,821,914 A * | 4/1989 | Owen et al. | .............. | 220/592.21 |
| 5,266,275 A | 11/1993 | Faddis | | |
| 5,275,668 A | 1/1994 | Dell et al. | | |
| 5,517,981 A | 5/1996 | Taub et al. | | |
| 5,520,893 A | 5/1996 | Kasting et al. | | |
| 5,667,753 A | 9/1997 | Jacobs et al. | | |
| 5,920,075 A | 7/1999 | Whitehead | | |
| 6,042,802 A | 3/2000 | Drake | | |
| 6,276,404 B1 * | 8/2001 | Birtcher et al. | ................... | 141/1 |
| 6,399,039 B2 | 6/2002 | Ostgard | | |
| 6,524,539 B1 * | 2/2003 | Katschnig et al. | ........ | 422/186.07 |
| 6,736,966 B2 | 5/2004 | Herrington | | |

* cited by examiner

*Primary Examiner* — Sean E Conley
*Assistant Examiner* — Regina M. Yoo
(74) *Attorney, Agent, or Firm* — Vin Ranucci

(57) ABSTRACT

A portable, lightweight, easy-to-carry, reusable, durable, and environmentally-friendly assembly for sterilizing contaminated equipment using conditions of a chemical sterilant, heat, and humidity generated in situ without requiring external electricity, fuels, or other exogenous energy sources for operation. The carry assembly includes a plastic carry-case or insulated aluminum pressure vessel having an inner chamber for accepting microbiologically contaminated objects, a vessel disposed in the chamber for serving as a reaction chamber and/or boiler, a chemical combination which upon mixing generates at least minimally sufficient conditions of the sterilant, heat, and humidity to effect sterilization of the objects, and outlet valves mounted on the carry-case for controllably venting pressures above ambient air pressure.

8 Claims, 4 Drawing Sheets

PORTABLE CHEMICAL STERILIZER

RELATED APPLICATION

This is a Divisional Application of U.S. patent application Ser. No. 11/105,211 filed Apr. 13, 2005 now U.S. Pat. No. 7,625,533, which is a continuation-in-part of U.S. patent application Ser. No. 10/988,442, filed Nov. 10, 2004 now U.S. Pat. No. 7,883,640. This Divisional Application claims priority under 35 U.S.C. 120 to the filing date of U.S. patent application Ser. No. 11/105,211, the entire teachings of which are incorporated herein by reference.

STATEMENT OF GOVERNMENT INTEREST

The invention described herein may be manufactured and used by the U.S. Government for governmental purposes without the payment of any royalty thereon.

BACKGROUND OF THE INVENTION

1. Field of the Invention

The present invention relates to lightweight, portable, self-contained devices whose operation does not require external power sources to sterilize assemblages of microbiologically contaminated equipment therein. The invention, more specifically, relates to such a device that uses chemical methods for sterilization and disinfection of equipment, such as medical and surgical instruments, in field conditions where water, electrical power, and/or fuel sources may be absent, unavailable, or of limited availability.

2. Description of the Prior Art

Far-Forward Army Surgical Teams currently have no existing technology for conveniently sterilizing surgical instruments on-site. Contaminated instruments are often transported with patients via aircraft to distant hospitals for sterilization in large steam autoclaves, and then returned enclosed in sterile packaging to the surgical teams via aircraft for re-use. Hospital steam autoclaves typically have 18-20 cubic foot chambers, weigh several hundred pounds, and require at a minimum permanent steam lines, water lines, and 110V electricity for operation.

Far-forward teams sometimes transport electric autoclaves into the field for carrying out sterilization. Electric autoclaves are smaller than hospital steam autoclaves, require some installation (such as 120 and 208-240 volt electrical lines), and consume significant amounts of water and power per sterilization cycle. For example, a typical sterilization cycle in an electric autoclave runs for 50-60 minutes and consumes about 1.5 gallons of potable water and approximately 12 kilowatts of power (at 236 volts). These electrical autoclaves are in fact difficult to transport in vehicles due to their weight (>100 lbs.), bulky dimensions, and reliance on generators or other power sources for operation.

Currently, there are no devices available for sterilizing surgical instruments that are portable, sufficiently lightweight (3-35 lbs.) to be easily hand-carried, do not require external power sources, such as electricity, and effect the sterilization process in 15-60 minutes.

In considering the design of a conveniently portable sterilizer, a choice must first be made as to which method, conventional moist heat, radiation, or chemical, will be the best to effect sterilization. Conventionally generated heat requires bulky autoclaves and significant amounts of power (usually electrical) to generate steam. Radiation requires a power supply or shielded enclosures, often both. Chemical methods have the potential to be conveniently portable, which has led to claims of portable disinfection, but not complete sterilization, and the chemical methods generally are not accomplished in convenient times as short as 15 minutes.

Chemical sterilization involves the use of controlled chemical processes to kill microbial contaminants by either i) directly transporting biocidal chemical agents in safety carriers, or ii) transporting the appropriate chemical precursors and chemically generating biocidal agents or sterilization conditions on-site, which often requires heavy-duty generating equipment. In these cases, it is important to distinguish the possibility of transporting chemicals or heavy-duty equipment in vehicles from a truly portable system. A truly portable system can be conveniently moved, lifted, or carried by the individual user, and includes the device, equipment, and chemicals involved in effecting the sterilization process.

Disinfectants such as chlorine, ethylene oxide, and fluorine-containing interhalogens are stable but highly reactive chemicals that must be transported in bulky, secure containers to ensure safety. While these chemicals can be transported, they are not truly portable because of their inconvenient weight and the safety precautions that must be taken to prevent accidents during shipping.

Many other potent chemical disinfectants are unstable and must be generated on-site from stable chemical precursors. The art of generating these chemical disinfectants has not been directed toward portability. For example, methods for generating disinfectants, such as hydrogen peroxide, ozone and chlorine gas, teach synthetic and electrochemical techniques that utilize heavy and bulky power supplies, solution reservoirs, fluid pumps, vacuum lines and other gas-handling systems. While this equipment can possibly be transported, it is not truly portable because of its large weight and size. Additionally, controlling this equipment requires electrical power and electrical circuitry, and transporting this equipment requires additional steps for removal and installation before operation can commence.

As indicated above, the established chemical methods currently being used to dispense or generate biocidal chemical agents or to chemically generate conditions for sterilization are not suited to lightweight portability. There is a need for a portable assembly for the sterilization or disinfection of microbiologically contaminated medical instruments, and the like, particularly one that involves using only a small amount (approximately 0.25 lb.) of safe, dry, chemical reagents. The chemical combination must be convenient to carry and mix with water readily to generate biocidal chemical agents or conditions sufficient for effecting sterilization.

Accordingly, an object of the invention is to provide such a portable apparatus adapted to use a chemical combination, and a number of variants thereof, that consist of mixtures of specially formulated iron-activated magnesium Mg(Fe) containing salt, sodium chlorite ($NaClO_2$), sodium sulfite ($Na_2SO_3$), and sodium hydrogen ascorbate ($C_6H_7O_6Na$) that react in water to controllably generate sterilization conditions inside the apparatus that include the production of biocidal chlorine dioxide, heat, and relative humidity.

Chlorine dioxide ($ClO_2$) is a potent, broad-based biocide that is effective against a wide variety of pathogenic microorganisms and bacterial spores. Chlorine dioxide is the EPA-registered disinfectant that was used to decontaminate the Hart Senate Office Building and the Brentwood postal facility in Washington, D.C. during the Anthrax attacks. In addition, chlorine dioxide is FDA-approved for disinfecting dental equipment and wastewater stores, and is used to kill pathogens and spoilage microorganisms that decrease the shelf-life of fresh and fresh-cut vegetables. Industrially, $ClO_2$ is produced from large chlorine dioxide generators and is used to treat wastewater and kill disease-carrying vectors, while protecting the environment by reducing the production of chlorinated organic by-products to very low levels compared with chlorine.

SUMMARY OF THE INVENTION

With the above and other objects in view, a feature of the present invention is the provision of a closable, portable (easy-to-carry), non-powered assembly for the sterilization of a collection of contaminated objects. This portable, power-free assembly accommodates controlled chemical reactions that generate in situ conditions of chemical sterilant, heat, and humidity sufficient to effect the sterilization of objects contaminated with microorganisms.

The assembly includes a closable apparatus defining an outer chamber having an inner chamber for accepting microbiologically contaminated objects, an interior vessel to act as a reaction chamber, a chemical combination that upon being mixed with water generates at least minimally sufficient conditions of chemical sterilant, heat, and humidity to effect sterilization, and valves dedicated to controllably preventing the accumulation of pressures above ambient air pressures and venting and deactivating chemical reaction products.

The preferred embodiment for this apparatus is a sterilization unit constructed from a plastic carry-case preferably weighing about 3.0-35 lbs, and of compact dimensions. The sterilization procedure entails placing the microbiologically contaminated equipment inside the carry case, combining the dry chemicals and water in a reactor vessel within the case, then closing and locking the case. Built-in outlet valves prevent the accumulation of excess pressure inside the case by allowing controlled release of heated gaseous products. An inlet valve is used to flow air into the apparatus after the sterilization process and expel gaseous products through the outlet valves.

In an alternative embodiment, the apparatus comprises a thermally insulated sterilizer unit with a vessel serving as a reaction chamber that is also called an internal boiler. This embodiment can be constructed from an aluminum vessel similar to a pressure cooker, preferably weighing about 17.5 lbs. and equipped with Teflon-covered foam insulation. The vessel is provided with a locking cover and is adapted to receive contaminated objects, and the internal boiler receives the dry chemicals and water. A vent pipe covered by a pressure regulator allows internal pressures to exceed atmospheric pressure to the extent needed for thermal sterilization. The vent pipe ensures user safety by releasing enough gas to prevent the internal pressure from becoming too high, and an accompanying dial gauge safely monitors the pressure. This embodiment is simply opened to expel gaseous products after the sterilization process, although it could be fitted with additional outlet and inlet valves to carry out flushing.

In general, the chemical combination used to effect sterilization is an ensemble of dry chemicals that react in water to controllably generate various levels of chlorine dioxide, heat, and relative humidity. The ensemble of dry chemicals consists of iron-activated magnesium {Mg(Fe)}, sodium chlorite ($NaClO_2$), sodium sulfite ($Na_2SO_3$), and sodium hydrogen ascorbate (chemical formula $C_6H_7O_6Na$ and designated with the symbol $AH^-$). Variants of the ensemble can be formulated by removing chemicals, or by adjusting the relative concentrations of the chemicals, and these systems are still capable of inactivating contaminating microorganisms.

When all of the dry chemicals are present and mixed together in water, the chemical combination generates large quantities of chlorine dioxide, heat, and humidity; we term this method "combined sterilization." Specifically, the combined sterilization method consists of Mg(Fe), $ClO_2^-$, $SO_3^{2-}$, and $AH^-$ mixed in water. In this case, the chemical combination produces copious amounts of chlorine dioxide, heat, and humidity, all of which act in concert to inactivate contaminating microorganisms.

A variant of the chemical combination can be formulated to generate large quantities of chlorine dioxide while concomitantly producing relatively low levels of heat and humidity; we term this method "chlorine dioxide sterilization." In chlorine dioxide sterilization, the chemical combination consists of $ClO_2^-$, $SO_3^{2-}$, and AR mixed in water (Mg(Fe) is excluded).

Another variant of the chemical combination generates large quantities of heat and humidity without producing chlorine dioxide; we term this method "thermal sterilization." In the thermal method, the Mg(Fe)—$H_2O$ reaction acts alone to produce substantial heat (Temperature$\geq 121°$ C.) and steam in the absence of $ClO_2$. In certain low temperature or high-altitude environments, the Mg(Fe)—$H_2O$ reaction can also contribute a source of heat to pre-warm or thaw the portable chemical sterilizer or frozen water.

The present invention provides for the removal of chlorine dioxide and other gases following the sterilization treatment. For outdoor environments the apparatus is simply opened to release the remaining sterilant gas.

For indoor environments, air flushing is used in conjunction with simple chemical methods to safely purge $ClO_2$ from the sterilization apparatus. Flowing air into the apparatus causes the expulsion of the chlorine dioxide gas through the outlet valves of the apparatus. The $ClO_2$ gas passes through specially designed scrubber devices engrafted onto these outlet valves, and common reductants embedded in the scrubber such as sulfite ($SO_3^{2-}$) dithionite ($S_2O_5^{2-}$), or thiosulfate ($S_2O_3^{2-}$) safely deactivate the chlorine dioxide gas. The reduction of $ClO_2$ occurs readily with these ions and these chemical reactions convert chlorine dioxide and the reductant to the environmentally safe and inert ionic products of chloride ($Cl^-$) and sulfate ($SO_4^{2-}$), respectively.

Additionally, chlorine dioxide features chlorine atoms in the +4 intermediate oxidation state (the oxidation states of chlorine range from −1 to +7). When chlorine dioxide comes in contact with a base such as sodium carbonate ($Na_2CO_3$), the chlorine dioxide can disproportionate into likewise environmentally benign, unreactive products chloride and chlorate ($ClO_3^-$).

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

DESCRIPTION OF THE PREFERRED EMBODIMENTS

Figure 1:
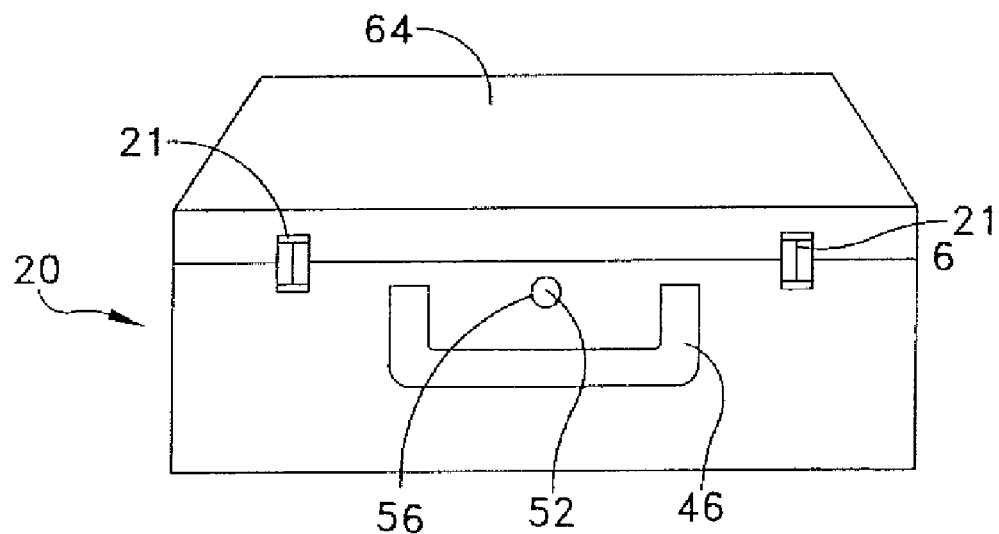
FIG. 1 is a front perspective view of one form of portable carry-case illustrative of the preferred embodiment of the invention.

The present invention is directed toward a lightweight, portable apparatus in the form of a convenient carry-case or handled vessel or box for carrying out chemical reactions that convert chemical energy to forms usable for the sterilization of microbiological contaminants without the use of external sources of power. Within the apparatus, sterilization is achieved in situ by chemically generating conditions involving a lethal steriilant, heat, and humidity, such that exposure of the contaminated objects to this environment sterilizes objects contaminated with harmful pathogens or infectious microorganisms.

The preferred use of the portable sterilizers includes using a chemical combination that ensures the complete destruction of contaminating microorganisms in an optimal time. Therefore, there follows below a detailed description of the chemical combination, followed by descriptions of the embodiments of the apparatus in which the chemical combination is activated to effectuate sterilization.

The chemical combination in the preferred method for sterilization is a mixture that can be decreased or increased proportionately, or that can be varied in the relative proportions of the components, depending on factors such as the size of the container in which sterilization is to occur or to emphasize different characteristics of the chemical combination. A representative chemical combination used for "combined sterilization" utilizes about 600 mL of water and the following approximate proportions of dry chemicals: 3.3 mole iron-activated magnesium (85 g Mg(Fe)), 2.04 mole chlorite ion (185 g $NaClO_2$), 1.0 mole sulfite ion (126 g $Na_2SO_3$), and 0.25 mole hydrogen ascorbate ion (50 g $NaC_6H_7O_6$). In one aspect designated "chlorine dioxide sterilization," the Mg(Fe) can be omitted from the chemical combination (300 mL $H_2O$, 93 g $NaClO_2$, 63 g $Na_2SO_3$, and 25 g $NaC_6H_7O_6$); in another aspect designated "thermal sterilization," only the Mg(Fe)—$H_2O$ chemical reaction (600 mL $H_2O$ and 140 g Mg(Fe)) is used, and the remaining 3 components of the chemical combination are omitted.

Alternative chemical combinations are also possible. For example, the magnesium can be activated by several different transition metals, such as cobalt or nickel. Other metallic reductants, such as calcium or sodium amalgam, can be used as simple substitutions.

The chlorine-containing oxidant ($ClO_2^-$) can derive from any one of several salts featuring different counter ions, such as lithium, sodium, potassium, or calcium cations. The hydrogen ascorbate salt acts as an effector and can be replaced by any appropriate effector such as ascorbic acid, erythorbic acid, tartaric acid, or any of their respective ions. Any chemical combination, such as those described in U.S. patent application Ser. No. 10/988,442, incorporated herein by reference, can be used. In the following description, reference will be made to the chemical combination used in the preferred embodiment, but this invention is not limited to the use of only this chemical combination and this preferred embodiment. Other reasonable substitutions for components of the chemical combination of the preferred embodiments, which produce equivalent chemical or microbiological processes, are obvious variants of the system described herein.

Figure 2:
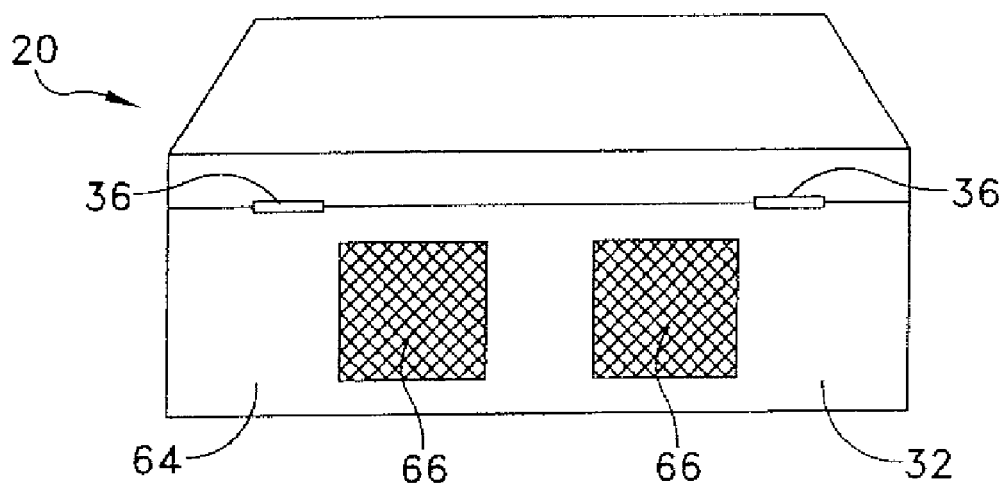
FIG. 2 is a rear perspective view of the case of FIG. 1.
Figure 3:
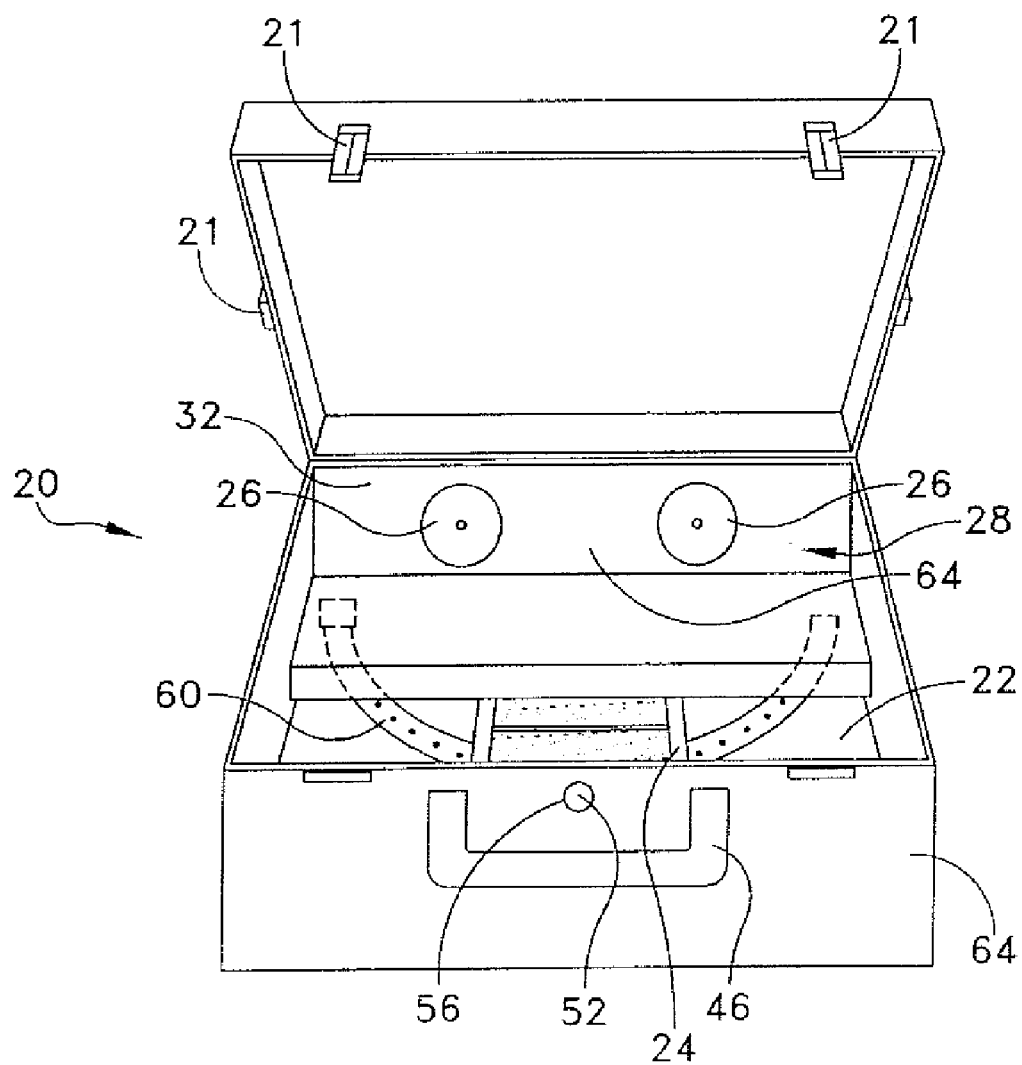
FIG. 3 is a front perspective view of the case of FIG. 1 with a top portion in an open position.
Figure 4:
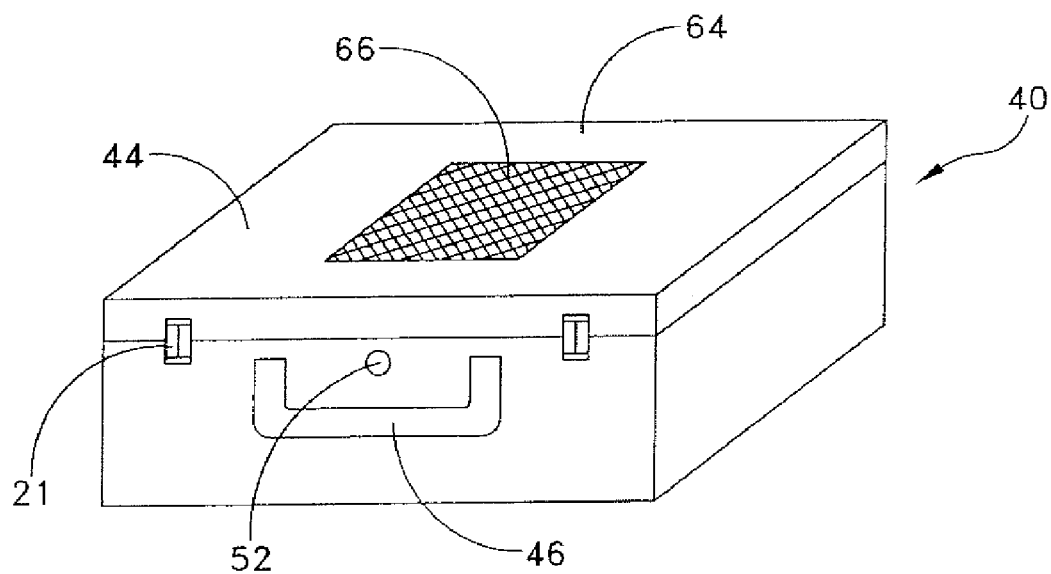
FIG. 4 is a perspective view of an alternative embodiment of a portable carry-case.
Figure 5:
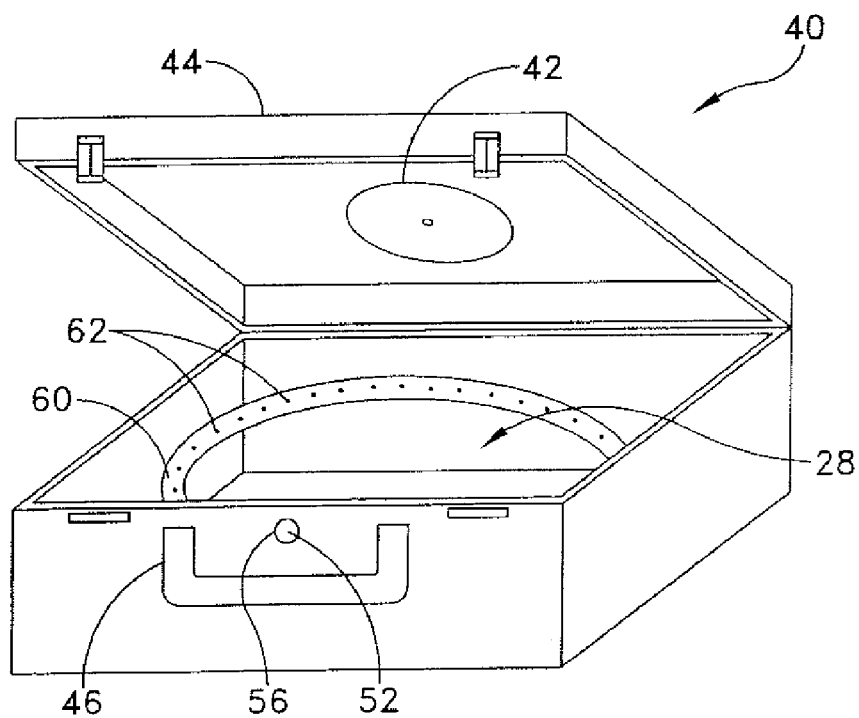
FIG. 5 is a perspective view of the case of FIG. 4, but shown with a top member in an open position.

Referring to FIGS. 1-3, it will be seen that a preferred embodiment of the present invention is a sterilizer unit that uses a carry-case 20 that has sufficient capacity to hold at least a standard surgical autoclave tray (not shown). The carry-case 20 preferably defines a volume of about 46 L. Two pressure-release check valves 26 (FIG. 3) are integrated into the back 32 of the case 20 using a protective framework (not shown) so that the valves 26 do not protrude beyond the structure of the carry-case 20, and do not interfere with stacking of the carry-cases. A smaller carry-case 40 defining a volume of about 3.5 L is shown in FIG. 4 and features the capacity to hold a loose assemblage of contaminated instruments. The smaller carry-case 40 features a single 2-inch check valve 42 (FIG. 5) installed in its roof 44. The valves 26, 42 are identical and are designed to withstand a maximum pressure of 50 psi (gauge). The carry cases 20, 40 typically weigh about 3½-35 lbs. and are provided with suitcase-handles 46, such that portability is readily facilitated.

The sterilization procedure for case 20 entails the simple steps of placing the microbiologically contaminated equipment (not shown) inside the case (28) on a support structure 22, adding the chemical combination (including water) in a small interior reactor vessel 24, and closing and locking the case 20, as with latches 21. A similar sterilization procedure is carried out for case 40.

Depending on the selected chemical reaction conditions, the corresponding chemical combination controllably generates sufficient conditions of $ClO_2$, heat, and humidity to sterilize the contaminating microorganisms within 15-120 minutes. Built-in pressure-release valves 26, 42 on cases 20 and 40, respectively, prevent pressure from accumulating inside the apparatus chambers (28 for both case 20 and 40, see FIGS. 3 and 5) by allowing the controlled release of heated gaseous products formed by the chemical combination.

The valves 26, 42 are initially in the closed position, but open to relieve pressure inside the chamber 28, 29 at minimal levels. The valves 26, 42 accommodate the initial rapid pressure increase in the interior chambers 28 of carry cases 20 and 40 caused by the rapid chemical production of gaseous chemicals, heat, and steam by the activated chemical combination. As a slight pressure builds up inside the cases from the formation of heated gases, the valves 26, 42 open slightly, and the heated gases vent outside of the cases through the opened valves. When the pressure has subsided sufficiently due to the escape of heated gases, the valves flap shut and return to their original closed position. During the early parts of the reaction with the preferred chemical combination, the pressure surges temporarily due to the chemical production of heated gaseous chemical products such as carbon dioxide ($CO_2$) and $ClO_2$, and the valves 26, 42 open to alleviate the pressure. As the pressure subsides, the valves close again.

After the sterilization (or disinfection) process is complete, the units 20, 40 may be flushed with air to remove the remaining $ClO_2$ gas. Following the air-flushing process, the user wears sterile gloves to open the case 20, 40 and remove the sterilized (disinfected) objects, which were preferably wrapped in autoclave paper prior to the sterilization process.

The sterilizer carry-case units 20, 40 are designed to control the removal of $ClO_2$ remaining after the sterilization procedure in the following manner. A stainless steel inlet valve 52 (for both case 20 and case 40) does not allow gases to flow out of the case. After the sterilization treatment, the inlet valve 52 is connected to an air pump (not shown) that inflows air into the case. A filter 56 is placed in the inlet valve 52 to prevent the introduction of air-borne particulate matter that might re-contaminate the sterilized objects. Any portable hand-held or foot-operated pedal pump may be used to flow air into the apparatus. There may be instances where it may be possible, desired, or advantageous to employ compressed air tanks or electrically operated air pumps to carry out the flushing procedure. Electricity or external power is in no case required to effect either the sterilization procedures or flushing of the apparatus; however, the carry-case sterilizer unit can accommodate battery-operated air pumps for flushing in circumstances where their use may prove convenient.

The incoming air is distributed within the carry-case units via 0.25 inch plastic tubing 60 disposed in a semi-circular (FIG. 3) or circular (FIG. 5) fashion around the interior perimeter of the carry-case. Perforations 62 in the plastic tubing 60 are spaced at approximately 1-inch intervals, allowing the incoming air to circulate throughout the carry-case and mix with the remaining chlorine dioxide gas. This influx of air slightly increases the pressure inside the apparatus chambers 28, and the mixture of air and chlorine dioxide gas flows out of the check valves 26 and 42, integrated into the back wall 32 of the carry-case 20 (FIG. 3) and into the roof 44 of the carry case 40 (FIG. 5), respectively. The valves 26, 42 open and close periodically to ensure that the gases mix and that the flushing operation proceeds smoothly and safely.

A gas scrubber 66 (FIG. 2 and FIG. 4) is connected to each check valve 26, 42 and absorbs the chlorine dioxide gas exiting the apparatus during any stage of the sterilization process, including flushing. Each scrubber 66 may consist of two layers of wire gauze (not shown) sandwiching a porous sponge material filled with a common reductant, such as sodium sulfite. The reductant readily inactivates the $ClO_2$ gas in the stream flow exiting the apparatus and safely limits user exposure and environmental off-gassing of $ClO_2$.

Figure 6:
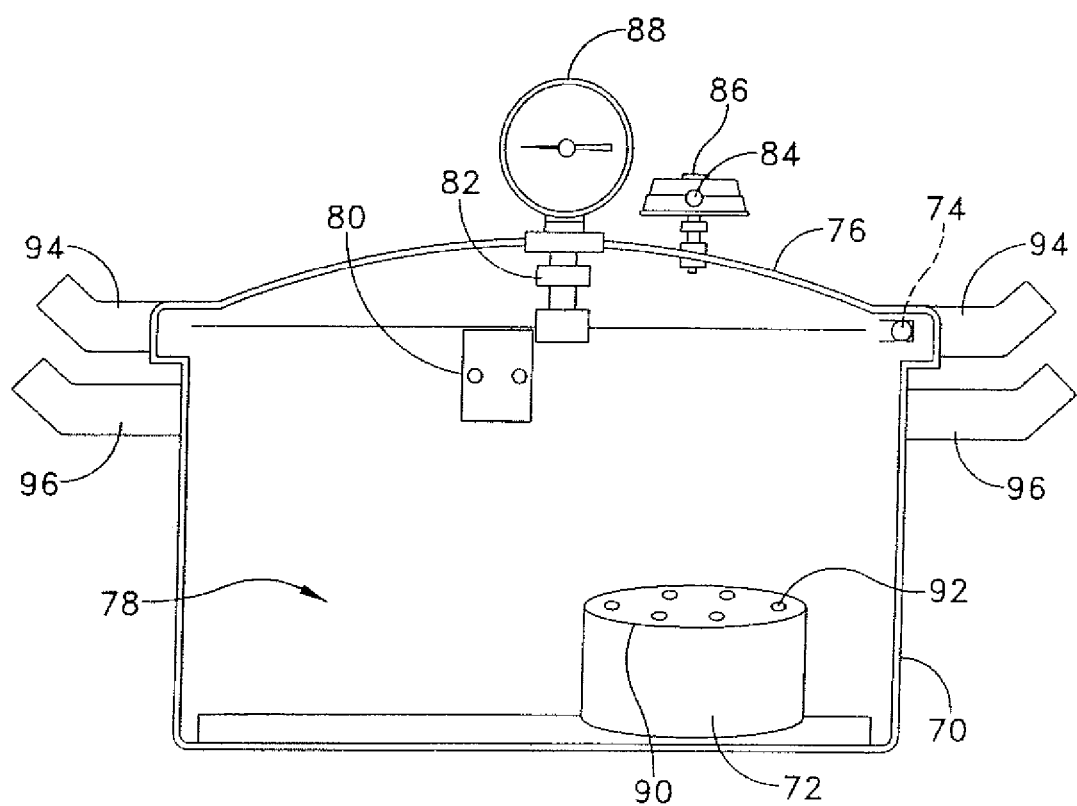
FIG. 6 is a side elevation view of a further alternative embodiment of a portable sterilizer.

An alternative embodiment of the present invention is an aluminum pressure vessel that is equally suited for non-powered, lightweight, portable sterilization of microbiologically contaminated objects by the in situ generation of sufficient conditions of chlorine dioxide, heat, and humidity using the chemical methods described above. This alternative embodiment (FIG. 6) of the sterilizer unit uses an aluminum pressure vessel 70 of about 20 liter capacity with its exterior covered in insulating foam and wrapped in a Teflon jacket, and its lid 76 snugly fitted with a sealing ring 74 and securely locked into place using brackets 80. An air vent 82 exhausts air from the pressurized vessel 70 and provides the first indication that heat and gases are building pressure inside the pressurized vessel. A vent pipe 84 covered by a pressure regulator 86 allows the controlled release of excess pressure, and an accompanying pressure gauge 88 registers the pressure inside the aluminum vessel chamber 78. The pressure vessel 70 typically weighs about 35 lbs or less, and is provided with handles 94 and 96, rendering the vessel 70 and lid 76 readily portable as a single, carryable unit.

Inside the pressurized aluminum vessel 70, an 1800 mL volume aluminum pot 90, of approximately 7 inch diameter, covered with a perforated lid 92 is placed at the interior base of the vessel to act as the internal boiler 72 and to allow for efficient mixing of the chemical combination. The apparatus in this arrangement is suitable for generating conditions capable of sterilizing microbiologically contaminated objects using various chemical combinations corresponding to the sterilization methods described above.

Using the pressurized aluminum vessel 70 to carry out "combined sterilization" is accomplished by either combining all of the reagents into the single boiler 72, or judiciously dividing the reactants into separate boilers (not shown). The heat output of the Mg(Fe)—$H_2O$ chemical combination is intensified by the presence of chlorite, peroxodisulfate, or copper(II) ions that also act to decrease the volume of dihydrogen gas produced by scavenging specific chemical precursors. With chlorite as the scavenger, the chemical combination is postulated to generate chlorine dioxide as an undetectable, short-lived reactive intermediate. The pressurized aluminum vessel 70 readily accommodates the methods of "chlorine dioxide sterilization" and "thermal sterilization." During "thermal sterilization," temperatures inside the pressurized vessel 70 can exceed 121° C.

After sterilization is complete for all of the chemical combinations, the aluminum pressure vessel 70 can be opened outdoors to release any gaseous chemical reaction products or heat to the environment, and the wrapped sterile instruments are removed using sterile gloves. The reaction vessel 72 is easily rinsed and cleaned, and the entire apparatus can be re-used on a new set of contaminated instruments.

It will be understood that many additional changes in the details, materials, and arrangement of parts, which have been herein described and illustrated in order to explain the nature of the invention, may be made by those skilled in the art within the principles and scope of the invention as expressed in the appended claims.

TEST RESULTS

A series of sterilization tests were conducted using commercially available biological indicators, live bacterial cells, or live bacterial spores to demonstrate the Portable Chemical Sterilizer using the presently available variants of hardware configurations and chemical combinations. Specifically, the sterilization tests used BT Sure Biological Indicator Tests for Steam Sterilizers (designated BT strips and available from Barnstead International, Dubuque, Iowa, USA), Difco Hy-check disinfection control for hygiene monitoring contact slides (designated Hy-check and available from Becton-Dickinson, Sparks, Md., USA), live cells of *Staphylococcus aureus* ($10^7$), *Escherichia coli* ATCC 11229 and 11220 ($10^7$ each), and *Listeria monocytogenes* ($10^6$), and live spores of *Bacillus stearothermophilus* ($10^8$).

Cultures were suspended in Butterfield's phosphate buffer solution and placed inside the Portable Chemical Sterilizer and exposed to the conditions of biocidal chemical agent, heat, and humidity generated by the chemical combination inside the apparatus. *S. aureus* was plated on Baird-Parker Agar supplemented with Egg-Yolk tellurite and incubated at 35° C. for 48 hours, both *E. coli* strains and *L. monocytogenes* were plated on Nutrient Agar and incubated at 35° C. for 24 and 48 hours, respectively, and *B. stearothermophilus* spores were plated on Antibiotic Assay Medium with 1% soluble Starch (AAMS) and incubated for 24 hours at 55° C. (F E Feeherry, D T Munsey, and D E Rowley 1987 Appl Environ Microbiol 53(2), 365-370). The results of the sterilization tests are shown in Tables 1-3.

TABLE 1

Sterilization tests in large plastic carry-case.
Negative results (−) indicate sterility.

| $ClO_2^-$ (g) | $SO_3^{2-}$ (g) | ascorbate (g) | water (mL) | Exposure time (min) | Results | Flush time (min) |
|---|---|---|---|---|---|---|
| 93 | 63 | 25 | 300 | 15 | −(BT strip in blue paper) | 15 |
| 140 | 94 | 37.5 | 450 | 15 | −(BT strip in blue paper) | 10 |

TABLE 1-continued

Sterilization tests in large plastic carry-case.
Negative results (−) indicate sterility.

| $ClO_2^-$ (g) | $SO_3^{2-}$ (g) | ascorbate (g) | water (mL) | Exposure time (min) | Results | Flush time (min) |
|---|---|---|---|---|---|---|
| 186 | 126 | 50 | 600 | 15 | −(BT strip in blue paper) | 15 |
| 93.12 | 63.12 | 25.02 | 300 | 24-15 | −(BT strip)<br>−(Hy-check)<br>−(wet live BT spores at 24 & 48 h)<br>−dry live BT spores | 15 |
| 102.48 | 69.4 | 27.82 | 300 | 15 | −Hy-check<br>−wet live BT spores at 24 & 48 h) | 15 |

TABLE 2

Sterilization tests in small plastic carry-case.
Negative results (−) indicate sterility.

| $ClO_2^-$ (g) | $SO_3^{2-}$ (g) | ascorbate (g) | water (mL) | Exposure time (min) | Results | Flush time (min) |
|---|---|---|---|---|---|---|
| 7.81 | 5.49 | 2.10 | 25 | 15 | −BT strip/ blue paper | 5 |
| 9.36 | 6.37 | 2.50 | 30 | 15 | −BT strip/ blue paper | 5 |
| 15.55 | 10.58 | 4.23 | 50 | 15 | −BT strip/ blue paper | 5 |
| 23.19 | 15.82 | 6.25 | 75 | 15 | −BT strip/ blue paper | 5 |
| 31.6 | 21.4 | 8.6 | 100 | 20-30 | −BT strip | 0 |
| 39.5 | 27 | 10.8 | 125 | 30 | −BT strip | 0 |

TABLE 3

Sterilization tests in a modified 20-Liter aluminum pressure vessel. Negative results (−) indicate sterility.

| $ClO_2^-$ (g) | $SO_3^{2-}$ (g) | ascorbate (g) | Mg/Fe (g) | water (mL) | Exposure time (min) | Results |
|---|---|---|---|---|---|---|
| 0 | 0 | 0 | 140 | 600 | 50 | − |
| 185 | 126 | 50 | 85 | 600 | 50 | − |
| 93 | 63 | 50 | 61 | 300 | 50 | − |
| 185 | 101 | 75 | 0 | 600 | 50 | − |
| 185 | 126 | 50 | 0 | 600 | 50 | − |
| 93 | 63 | 75 | 0 | 300 | 50 | − |
| 93 | 63 | 75 | 0 | 300 | 50 | − |
| 46.5 | 31.5 | 12.5 | 0 | 300 | 50 | − |
| 46.5 | 31.5 | 12.5 | 0 | 150 | 50 | − |
| 23.3 | 31.5 | 12.5 | 0 | 150 | 50 | − |
| 186 | 126 | 50 | 0 | 600 | 15 | − |
| 140 | 94 | 37.5 | 0 | 450 | 15 | − |
| 93 | 63 | 25 | 0 | 300 | 15 | − |
| 93 | 63 | 25 | 0 | 300 | 15 | − |
| 93 | 63 | 50 | 0 | 300 | 15 | − |
| 46.5 | 31.5 | 12.5 | 0 | 300 | 50 | live SA, EC, LM. BT |

What is claimed is:

1. An assembly for sterilizing of a plurality of microbiologically contaminated objects, using in situ generated heat and humidity, the assembly comprising:

a unit comprising a closable, portable, hand carried carry case weighing up to about 35 pounds and having an inner chamber for accepting microbiologically contaminated objects;

an interior vessel disposed in the inner chamber for serving as a reaction chamber, said vessel for receiving and combining dry chemical precursors with water, within the case, said vessel being adapted for rinsing and cleaning, independently from the case, for reusing the vessel on other contaminated objects;

a combination of dry chemical precursors which upon combining with water generates in situ at least minimally sufficient conditions of heat and humidity to effect microbiological sterilization of the objects, said combination of dry chemicals excluding acids and consisting of chlorite ion, sulfite ion, and hydrogen ascorbate ion combined with water for producing chlorine dioxide, heat and humidity in amounts sufficient to effect said sterilization, under which reaction by electron transfer the ascorbate initiates a reduction of chlorite by a transfer of an electron form chlorite to ascorbate for causing a release of heat, a decrease in solution pH, and a release of chlorine dioxide in heated gaseous and aqueous forms, said reaction between ascorbate and chlorite inducing chemical reaction between chlorite and sulfite for producing heat and increasing solution pH for generating heated chlorine dioxide at neutral pH for affecting said objects to expose any contaminating microorganisms to said chlorine dioxide and sterilizing said objects; and a pressure release outlet valve mounted on said unit for automatically controlling pressures at ambient during sterilization;

wherein the assembly, including the unit, vessel, combination of dry chemical precursors with water, and outlet valve is self-contained, reusable and is free of any external source of power for controllably generating sufficient amounts of heat and humidity to sterilize the contaminated objects.

2. The assembly in accordance with claim 1, wherein said unit comprises a generally rectangular-shaped bottom wall, four side walls respectively upstanding from side edges of said bottom wall, and a top wall pivotally mounted on one of said side walls and adapted to be moved between an open position and a closed position so as to define, in conjunction with said bottom wall and said side walls, the inner chamber, said vessel being placed in the inner chamber and adapted to receive said combination of dry chemical precursors for combining with water, and a support structure for receiving and supporting the contaminated objects and said outlet valve being mounted in at least one of said walls.

3. The assembly in accordance with claim 1 wherein said unit comprises insulated aluminum.

4. The assembly in accordance with claim 1 wherein said chemical combination comprises about 600 mL $H_20$, 185 g $NaCl0_2$, 126 g $Na_2S0_3$, and 50 g $NaC_6H_70_6$.

5. The assembly in accordance with claim 1 wherein said unit comprises a plastic.

6. The assembly in accordance with claim 1, wherein said combination of chemical precursors and water is varied in relative proportions of chemical components depending on size of unit in which sterilization occurs.

7. The assembly in accordance with claim 1, wherein said combination of chemical precursors and water is varied in relative proportions of chemical components depending on different characteristics of the combination of chemicals.

8. The assembly in accordance with claim 1, wherein said pressure release outlet valve comprises a vent pipe and a pressure regulator.

* * * * *